(12) United States Patent
McPherson et al.

(10) Patent No.: US 9,204,920 B2
(45) Date of Patent: Dec. 8, 2015

(54) EXTERNAL READER FOR DEVICE MANAGEMENT

(75) Inventors: James W. McPherson, Boulder, CO (US); D. Alan Hanna, Westminster, CO (US)

(73) Assignee: Covidien LP, Mansfield, MA (US)

( * ) Notice: Subject to any disclaimer, the term of this patent is extended or adjusted under 35 U.S.C. 154(b) by 852 days.

(21) Appl. No.: 13/462,348

(22) Filed: May 2, 2012

(65) Prior Publication Data
US 2013/0293353 A1  Nov. 7, 2013

(51) Int. Cl.
G08B 13/14 (2006.01)
A61B 18/12 (2006.01)
A61B 19/02 (2006.01)
A61B 19/00 (2006.01)

(52) U.S. Cl.
CPC ........... *A61B 18/1206* (2013.01); *A61B 19/026* (2013.01); *A61B 19/44* (2013.01); *A61B 2019/0267* (2013.01); *A61B 2019/442* (2013.01); *A61B 2019/448* (2013.01)

(58) Field of Classification Search
None
See application file for complete search history.

(56) References Cited

U.S. PATENT DOCUMENTS

| | | | |
|---|---|---|---|
| 4,827,927 A | 5/1989 | Newton | |
| 5,353,929 A | 10/1994 | Foster | |
| 5,359,993 A | 11/1994 | Slater et al. | |
| 6,519,569 B1 | 2/2003 | White et al. | |
| 7,131,860 B2 | 11/2006 | Sartor et al. | |
| 7,184,820 B2 | 2/2007 | Jersey-Willuhn et al. | |
| 7,651,493 B2 | 1/2010 | Arts et al. | |
| 7,839,674 B2 | 11/2010 | Lowrey et al. | |
| 7,842,033 B2 | 11/2010 | Isaacson et al. | |
| 7,900,805 B2 | 3/2011 | Shelton, IV et al. | |
| 7,901,400 B2 | 3/2011 | Wham et al. | |
| 2002/0067264 A1* | 6/2002 | Soehnlen | 340/572.1 |
| 2002/0165541 A1 | 11/2002 | Whitman | |
| 2005/0113815 A1 | 5/2005 | Ritchie et al. | |
| 2005/0113818 A1 | 5/2005 | Sartor et al. | |
| 2005/0203504 A1 | 9/2005 | Wham et al. | |

(Continued)

FOREIGN PATENT DOCUMENTS

| | | |
|---|---|---|
| EP | 1772109 | 4/2007 |
| EP | 1997439 | 12/2008 |

(Continued)

OTHER PUBLICATIONS

International Search Report and Written Opinion of the International Searching Authority corresponding to International Application No. PCT/US2013/036699, dated Sep. 16, 2013; 9 pages.

*Primary Examiner* — Firmin Backer
*Assistant Examiner* — Brian Wilson

(57) ABSTRACT

A system for tracking use of a medical device including an electrosurgical generator, a readable module and a read module. The electrosurgical generator is configured to selectively deliver an electrosurgical energy signal to an electrosurgical delivery device connected to the electrosurgical generator. The readable module is connected to the electrosurgical delivery device and configured to uniquely identify the electrosurgical delivery device. The read module is in communication with the electrosurgical generator that identifies the read module, the read module configured to identify the readable module and further configured to determine the viability of the electrosurgical delivery device. Delivery of electrosurgical energy to the electrosurgical delivery device is enabled by the read module if the electrosurgical delivery device is a viable device.

13 Claims, 3 Drawing Sheets

(56) References Cited

U.S. PATENT DOCUMENTS

| | | |
|---|---|---|
| 2006/0079881 A1 | 4/2006 | Christopherson et al. |
| 2007/0016185 A1* | 1/2007 | Tullis et al. ............... 606/41 |
| 2007/0024445 A1* | 2/2007 | Weslake et al. ........... 340/572.1 |
| 2007/0035383 A1* | 2/2007 | Roemerman et al. ........ 340/10.1 |
| 2007/0060919 A1 | 3/2007 | Isaacson et al. |
| 2007/0060921 A1* | 3/2007 | Janssen et al. ............... 606/41 |
| 2007/0208339 A1 | 9/2007 | Arts et al. |
| 2007/0233065 A1 | 10/2007 | Donofrio et al. |
| 2007/0244825 A1 | 10/2007 | Semmer et al. |
| 2008/0211634 A1 | 9/2008 | Hopkins et al. |
| 2008/0300580 A1 | 12/2008 | Shelton, IV et al. |
| 2009/0054889 A1 | 2/2009 | Newton et al. |
| 2009/0065565 A1* | 3/2009 | Cao ............................. 235/375 |
| 2009/0076534 A1 | 3/2009 | Shelton, IV et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0177094 A1 | 7/2009 | Brown et al. |
| 2009/0248007 A1* | 10/2009 | Falkenstein et al. ............ 606/33 |
| 2010/0076483 A1* | 3/2010 | Imuta ............................ 606/205 |
| 2010/0213255 A1* | 8/2010 | Yoo ................... G06K 19/06046 235/449 |
| 2010/0286691 A1 | 11/2010 | Kerr et al. |
| 2011/0270250 A1 | 11/2011 | Horner et al. |
| 2011/0270252 A1 | 11/2011 | Horner et al. |
| 2012/0241515 A1* | 9/2012 | Freeman ........... G06K 19/06037 235/375 |

FOREIGN PATENT DOCUMENTS

| | | |
|---|---|---|
| EP | 2 113 864 A2 | 4/2009 |
| WO | WO 02/085218 | 10/2002 |
| WO | WO 2006/036372 A1 | 4/2006 |
| WO | WO 2009/035886 A1 | 3/2009 |
| WO | WO 2009/039510 | 3/2009 |

\* cited by examiner

EXTERNAL READER FOR DEVICE MANAGEMENT

BACKGROUND

1. Technical Field

The present invention relates to systems and methods for performing a medical procedure, wherein the systems and methods record and tract the usage of single use and reusable medical devices.

2. Description of Related Art

The use of electrosurgical instruments is well known in the art. Electrosurgical instruments typically utilize both mechanical clamping action and electrical energy to affect hemostasis by heating the tissue and blood vessels to coagulate, cauterize and/or seal tissue. Over the course of a surgical procedures a clinician may use a variety of electrosurgical instruments such as, for example, elongated electrosurgical forceps to cauterize, coagulate/desiccate and/or to simply reduce or slow bleeding in a surgical cavity, electrosurgical pencil or scalpel for cutting or to cauterize a surgical opening, an electrosurgical vessel sealing device including actuating jaw members of an end effector assembly for sealing and cutting vessels. In addition to the assortment of electrosurgical instruments available to a clinician, many electrosurgical instruments are configured to receive a variety of attachments or members, such as tips, jaws, blades, electrode configurations or combination thereof.

During the course of a surgical procedure, a clinician may employ a variety of different instrumentation, including reusable instruments, limited use reusable instruments, and disposables instrument. Reusable instruments are instruments where the reusability of the instrument is limited only by operability of the instruments (e.g., proper operation, recommended maintenance and/or reconditioning schedules). A limited use reusable instrument includes instruments with a limited useful life, wherein the useful life of the instrument may be based the number of electrical activations, the cumulative time of electrical activation, the number of mechanical activations, the number of surgical procedures performed or any combination thereof. A disposable instrument is an instrument intended to be introduced to a surgical field, used for its intended purpose and immediately disposed of thereafter.

Instruments may also be configured to receive a disposable or limited use attachment or member. For example, a reusable electrosurgical scalpel may be configured to receive a limited use or disposable blade or a limited use reusable vessel sealing device may be configured to receive a disposable single-use shaft and end effector or end effector assembly or jaw assembly.

A manufactures' "limited use" or "disposable" recommendation is typically based on performance testing, reliability testing, the inability to properly sterilize the instrument or attachment member using conventional sterilizing techniques, the material degradation as a result of conventional sterilization techniques or any combination thereof. A clinician must know the use limitation, track the actual usage and abide by the instructions by disposing of the instrument after the actual usage has been exceeded. In some instances there may be a temptation to re-use disposable instruments or use items beyond the recommended useful life to save costs especially in clinic-type environments or low-income areas. Obviously, health issues and concerns arise when disposable instruments are re-used for surgical purposes or when instruments are used beyond their recommended life or cycles. As such, the use recommendation for reusable or disposable members sometimes depends on the clinician, surgeon or surgical personnel to discard the instrument or member after the manufactures' recommended number of uses is exceeded.

To assist clinicians in abiding by a manufacturer's intended use and disposal instructions, and to prevent intentional re-use of instruments, manufactures have employed a number of systems and methods. For example, to prevent accidental reuse, some instruments are packaged such that the packaging is destroyed when opened. Other instruments employ smart-connectors to prevent reconnection and reuse of a particular instrument with the same electrosurgical generator. Other instruments have employed a time-out device configured to prevent re-use of the electrosurgical instrument after a predetermined time limit.

The present disclosure describes devices and systems that interface with an existing electrosurgical generator, or the like, to record and track the usage of single use and reusable medical devices.

SUMMARY

The present disclosure relates to a system for tracking use of a medical device, including an electrosurgical generator configured to selectively deliver an electrosurgical energy signal, an electrosurgical delivery device configured to connects to the electrosurgical generator and receives the electrosurgical energy signal therefrom, a readable module connected to the electrosurgical delivery device and configured to uniquely identify the electrosurgical delivery device; a read module in communication with the electrosurgical generator and configured to identify the read module, the read module configured to identify the readable module and further configured to determine the viability of the electrosurgical delivery device, wherein delivery of the electrosurgical energy to the electrosurgical delivery device is enabled by the read module if the electrosurgical delivery device is a viable device.

Another aspect of the system includes a device tracking and management system in communication with the read module and configured to provide information specific to the uniquely identified electrosurgical delivery device to the read module. The read module may determine the viability of the electrosurgical delivery device based on the information specific to the uniquely identified electrosurgical delivery device provided from the device tracking and management system. The read module may provide information relating to the electrosurgical generator to the device tracking and management system. The device tracking and management system may include a billing module configured to generate a per use bill based on the information related to the electrosurgical generator provided by the read module. The device tracking and management system may includes an inventory control module configured to maintain product inventory based on the information related to the electrosurgical generator provided by the read module.

According to a further aspects of the disclosure, the readable module includes a bar code, and the read module includes a scanner configured to identify the bar code. The readable module may also include a radio frequency identification module and the read module may also include a scanner configured to identify the radio frequency identification module.

According to other aspects of the disclosure, the readable module includes a readable module wireless communication device and the read module includes a read module wireless communication device configured to wirelessly communicate with the readable module wireless communication device. The readable module may also include memory accessible by the read module when the read module electrically connects to the memory.

BRIEF DESCRIPTION OF THE DRAWINGS

Various aspects of the present disclosure are described hereinbelow with reference to the drawings, wherein.

DETAILED DESCRIPTION

Figure 1:
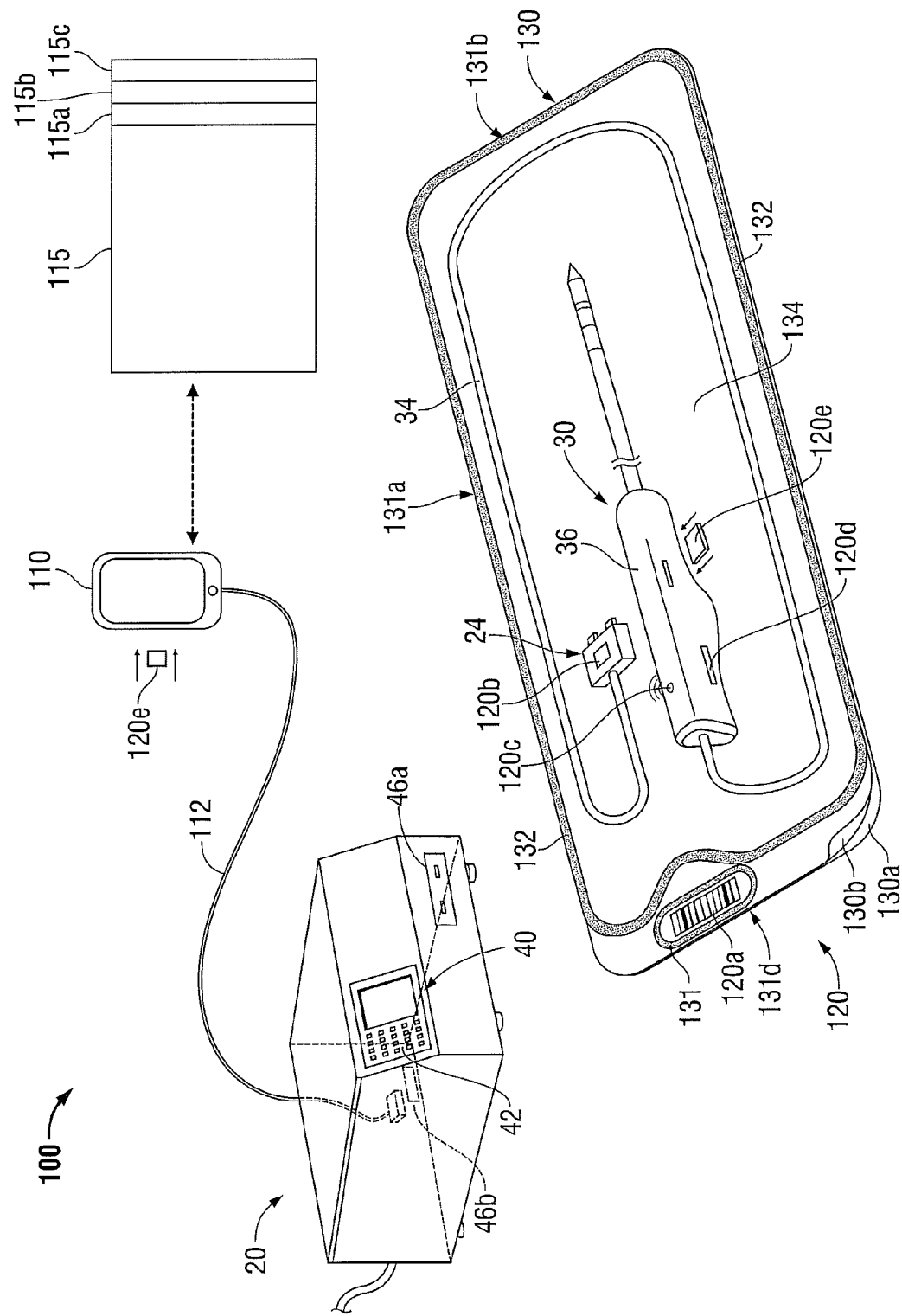
FIG. 1 is a perspective view of an electrosurgical system utilizing an external usage tracking system according to an embodiment of the present disclosure.

Detailed embodiments of the present disclosure are described herein; however, it is to be understood that the disclosed embodiments are merely exemplary and may be embodied in various forms. Therefore, specific structural and functional details disclosed herein are not to be interpreted as limiting, but merely as a basis for the claims and as a representative basis for teaching one skilled in the art to employ the present disclosure in virtually any appropriately detailed structure.

In the drawings and in the descriptions that follow, the term "proximal," as is traditional, will refer to an end which is closer to the user, while the term "distal" will refer to an end that is farther from the user.

Generally, the systems and methods described herein are related to an external usage tracking system that includes a readable module and one or more read modules for preventing and/or tracking use of a reusable and/or disposable instrument. A read module is associated with an instrument and may be incorporated into, and/or affixed to, an instrument, the packaging of the instrument or both. The read module interfaces with each readable module and receives one or more identifying characteristic of the associated instrument from the read module. The identifying characteristics are used to determine the viability of the instrument and read module provides the viability of the instrument to a system that interconnects and/or interfaces with the instrument. The viability of the instrument may be related to system compatibility and/or connectability, related to a prior use, related to an expiration date and/or timeframe, or related to any other suitable measure or criteria.

Referring now to FIG. 1, an electrosurgical system for supplying electrosurgical energy for a medical procedure including an external usage tracking system 100 according to an embodiment of the present disclosure, is shown as 10. The electrosurgical system 10 includes an electrosurgical generator 20, a delivery device 30 configured to couple to the electrosurgical generator 20 via a transmission line 34 and an external usage tracking system 100.

The electrosurgical system 10 is provided and described to demonstrate the use and features of an external usage tracking system 100. This specific example should not be construed as limiting. The external usage tracking system 100 may be used with any system that utilizes disposable and/or limited use components such as, for example, systems that utilize disposable end effectors (e.g., radiofrequency systems, microwave systems and/or ultrasonic systems), and systems that utilize disposable cartridges (power-staplers, printers, copiers, power nail driver, and/or a CO2 cartridge actuated device).

Electrosurgical generator 20 may include an operator interface 40 having a keypad 42 for entering parameters related to electrosurgical generator 20, the delivery device 30 and/or parameters related to the operation thereof. Display 44 may indicate or graph one or more parameters related to the surgical procedure, the electrosurgical generator 20, the transmission line 34 and/or delivery device 30 and/or the external usage tracking system 100. Electrosurgical generator 20 includes a central processing unit and control circuit (not explicitly shown) for controlling the operation of the electrosurgical generator 20.

Delivery device 30 may be any suitable electrosurgical delivery device such as, for example, a radio-frequency, microwave, and/or ultrasonic ablation device, a tissue-sealing device or other electrosurgical tissue treatment device, or delivery device 30 may be a component delivery device such as a power-stapler, power-nail driver, printer or copier. Delivery device 30 may be a single-use disposable device, a multi-use disposable device or a limited use reusable device.

Transmission line 34 may be a coaxial cable (i.e., a waveguide), a multi-conductor cable or any other suitable cable or combination thereof for transmitting an electrosurgical energy signal and/or electrosurgical control signals. Connector 24 disposed on the proximal end of the transmission line 34 couples to a transmission line receiver 46 on the electrosurgical generator 20. A distal end of the transmission line 34 connects to the handpiece 36 of the delivery device 30.

External usage tracking system 100 includes a read module 110, one or more readable modules 120 and a remotely-located device tracking and management system 115. The various components of the external usage tracking system 100 cooperate to track and record the usage of each specific delivery device 30 as described hereinbelow.

Read module 110, as illustrated in FIG. 1, connects directly to the electrosurgical generator 20 through a read module cable 112. The read module cable 112 may connect directly to a preexisting communication port 46b in the electrosurgical generator 20 and may use any suitable communication protocol to communicate with the electrosurgical generator 20. Alternatively, read module 110 may connect to an analog or digital input port on the electrosurgical generator 20 and may provide an analog or digital signal that provides information and/or data related to or from the external usage tracking system 100. One suitable communication protocol may include a wireless protocol (e.g., Wi-Fi, Bluetooth, ZigBee or other suitable wireless communication protocol) wherein the read module 110 wirelessly connects to the electrosurgical generator 20.

In some embodiments, the read module 110 is a smart device configured to execute one or more applications related to the external usage tracking system 100. The one or more applications may be related to controlling a scanner housed in the read module 100 and configured to read/identify a readable code formed by the readable module 120. For example, one application may control an optical reading device (e.g., camera/bar code scanner) configured to identify/read the readable code. The readable code may be a one-dimensional bar code, a two-dimensional bar code or any optically distinguishable and/or identifiable pattern. A readable code and a bar code may be used interchangeably herein. Read module 110, in addition to communicating with the device tracking and management system 115, may include an application configured to communicate with individual read modules 110 thereby forming a localized network between pluralities of read modules 110. In some embodiments, read module 110 is a wireless pistol grip reader.

In another embodiment, the read module 110 functionality described herein is incorporated into the circuitry of a new electrosurgical generator 20. As such, the particulars of the electrosurgical generator 20, delivery device 30 and external usage tracking system 100, and the interaction of the various components illustrated in the figures and described herein, may be distributed between the electrosurgical generator 20, the delivery device 30 and other components of the external usage tracking system 100. As such, the system and methods described herein are provided only as examples and should not be construed as limiting.

Read module 110 is configured to interface with one or more readable modules 120 associated with a specific delivery device 30. Readable modules 120 are read and/or detected by the read module 110 and may include any suitable readable and/or detectable technologies. For example, readable module 120 may include a readable identification code such as, for example, a one-dimensional bar code 120a, a two-dimensional bar code 120b or any other suitable readable identification pattern, device or coding.

Readable module 120 may also include a hard-wired readable technology such as, for example, an EEPROM, microcontroller or smart card 120e. Read module 110 may connect to the readable module 120 by a suitable electrical cable (not explicitly shown) or readable module (e.g., smart card 120e) may be removed from the delivery device 30 and connected to the read module 110. Information related to the delivery device 30 is transferred between the read module 110 and the readable module 120 via the readable module (e.g., smart card 120e).

Readable module 120 may also connect to the read module 110 via a wireless communication system (e.g., wireless transmitter/receiver 120c). Wireless transmitter/receiver 120c may connect by any suitable low-power wireless digital communication protocols, such as, for example, Bluetooth or ZigBee. Read module 110 may be configured to automatic detect a delivery device 30 with a wireless transmitter/receiver 120c when a delivery device 30 is positioned proximate to the read module 110. Alternatively, a wireless connection may be manually initiated by a clinician.

Readable module 120 may also connect to the read module 110 via a detectable technology such as, for example, a radio frequency identification device (RFID) 120d. Read module 110 may detect the readable RFID module 120d positioned on (or within) the delivery device 30 after the delivery device 30 is positioned proximate the read module 110. The readable RFID module 120d connected to the delivery device 30 may be automatically detected the by the read module 110 or detection thereof may be manually initiated by a clinician.

In use, the read module 110 receives identification information from one or more readable modules 120a-120e positioned on a specific delivery device 30 or positioned on the packaging material 130 that house the delivery device 30. The read module 110 connects to the device tracking and management system 115 via a direct or indirect connection (e.g., a wi-fi or wireless connection) and provides the identification information thereto.

The device tracking and management system 115 utilizes the identification information to locate tracking and usage information related to the specific delivery device 30. The tracking and usage information is used to determine if the specific delivery device 30 is a viable device (e.g., reusable and/or unused device), a compatible device (e.g., compatible to the specific electrosurgical generator 20) and/or a device that is safe to use (e.g., no manufacturing recalls). The determination step may be performed by the device tracking and management system 115, the read module 110, the electrosurgical generator 20 or any combination thereof.

New information (or changes to existing information) may be related to the use of the electrosurgical generator 20 with the specific delivery device 30. The new information, or changes to the existing information, may be added to the corresponding record in the device tracking and management system 115 before, during and/or after the delivery device 30 is used. The information may include time-stamped information, information related to the electrosurgical generator 20, read module 110 and readable module 120, information related to the surgical procedure (e.g., type, duration, etc. . . . ), information related to performance and/or delivered energy and information related to the user and/or facility (e.g., an operator entered facility code or location codes).

Device tracking and management system 115 tracks one or more aspects of a specific delivery device 30. For example, device tracking and management system 115 may track the usage of a single-use delivery device and may further prevent the re-use of the single-use delivery devices 30. Device tracking and management system 115 may also track the use and reuse of a specific reusable delivery device 30 and may prevent re-use of the specific reusable delivery device 30 if the specific use is determined to be an unsafe or not permitted. Device tracking and management system 115 identifies each specific delivery device 30 during or after manufacturing, associates the readable devices 120 with the specific delivery device 30, tracks each specific delivery device 30 throughout its usable life, and prevents reuse after the usable life has expired.

Device tracking and management system 115 may also be configured to include the functionality of an enterprise resource planning system. For example, a component of the device tracking and management system 115 may include an inventory control module 115a for tracking and controlling inventory for a specific office, hospital and/or a specific storage location therein. Inventory control module 115a of the device tracking and management system 115 may automatically generate orders based on usage and/or availability or may provide order recommendations based on historic usage.

Device tracking and management system 115 may also include a sterilization control module 115b to provide sterilization monitoring and tracking. In some embodiments, sterilization control module 115b of the device tracking and management system 115 tracks, records and/or monitors each individual use and subsequent sterilizations that occur after each of the uses. Device tracking and management system 115 may prevent a specific delivery device 30 from re-entering an inventory system if time-stamp information indicates that sterilization was not performed, indicates with a high degree of likelihood that sterilization was not adequately performed or indicates that sterilization was bypassed altogether. For example, time-stamp information from the electrosurgical generator 20 may indicate that a specific delivery device 30 was being reintroduced into inventory directly after an indicated use, thereby indicating that sterilization could not have been performed.

Device tracking and management system 115 may also include a billing module 115c that generates automated customer billing (for single use and/or limited-use reusable delivery devices) and/or automated patient billing (for single use devices, pay-per-use devices and/or split billing for payper-use or reusable devices). For example, in a surgical procedure a read module 110 identifies a specific delivery device 30 and reports the use to the device tracking and management system 115. If the specific delivery device 30 is a single use device, the inventory control module 115a would initiate a reorder for a new delivery device and the billing module 115c would initiate appropriate patient billing for use of the delivery device 30. If the specific delivery device 30 is a limited use reusable device, the inventory control module 115a may initiate a reorder of the delivery device 30 if the use tracking indicates the delivery device 30 has expired and the delivery device 30 can not be reused. The billing module 115c generates appropriate patient billing for the allocated percentage of use of the delivery device 30 and an order may be initiated by the inventory control module 115a.

External usage tracking system 100 is configured to interface with the electrosurgical control algorithm that controls the operation of the electrosurgical generator 20. In some embodiments, the electrosurgical control algorithm in an existing electrosurgical generator 20 is reprogrammed to connect to the read module 110 through a pre-existing communication port 46b. As such, implementation of an external usage tracking system 100 may be accomplished by implementing a software upgrade of the electrosurgical control algorithm in an existing electrosurgical generator 20 and connecting the read module 110 to the electrosurgical generator 20.

New electrosurgical generators may be configured to connect to a read module 110 of the external usage tracking system 100 through any suitable wireless personal area network (WPAN) such as, for example, Bluetooth, infrared or WiFi, therefore requiring minimal changes to implement an external usage tracking system 100.

The information provided to the electrosurgical generator 20 from the read module 110 may include information related to the manufacturing, assembly and testing of the delivery device 30, information related to use of the delivery device 30 and/or information related to the compatibility of the delivery device 30 with the electrosurgical generator 20. The information may also be related to the safe operation of the delivery device 30 and may include safe operating procedures, product recall information and/or information about the delivery device 30 and/or materials used to manufacture the delivery device 30 that were obtained after the delivery device 30 was manufactured.

The external usage tracking system 100 may provide the read module 110 with product performance information related to the specific delivery device 30 such as delivery device 30 specifications and test data. As can be appreciated, identification of the specific delivery device 30 by the external usage tracking system 100 provides the capability of providing up-to-date information related to the specific delivery device 30.

In another embodiment, the information provided to the electrosurgical generator 20 from the read module 110 may be limited to enabling and/or disabling when the read module 110 and/or the device tracking and management system 115 (or any component thereof) determines if the specific delivery device 30 has expired. The read module 110 provides an enable/disable signal to the electrosurgical generator 20 wherein providing an enable signal indicates that the delivery device 30 is a viable device (e.g., unused and/or capable of being reused), a compatible device, an unexpired device and/or any combination thereof. The enable signal may enable delivery of the electrosurgical energy to the delivery device 30.

New delivery device platforms may include new features designed for connecting and interfacing with new electrosurgical generators. As such, the new delivery device platforms are incompatible with the early generation electrosurgical generators 20. For example, a new delivery device platform may include features related to an external usage tracking system 100 that had not been included in early generation electrosurgical generators. As such, read module 110 may be configured to interface with the features included in the new delivery devices platform (e.g., wireless communication transmitter/receiver 120c as will be discussed in more detail herein). As such, an electrosurgical system 100 with an early generation electrosurgical generator 20 may utilize the new platform features provided in or with a new delivery device 30 platform by interfacing with the early generation electrosurgical generator 20 through the read module 110.

Returning to FIG. 1, the delivery device 30 is configured to interface with the external usage tracking system 100. Delivery device 30 includes a plurality of readable modules 120 configured to interface with the readable module 110. FIG. 1 illustrates several readable modules 120 although as few as one readable module 120 may be used.

In some embodiments, read module 120 is incorporated into the packaging materials 130 (e.g., one-dimensional bar code 120a formed in the soft-pack 130), incorporated into the connector 24 on the proximal end of the transmission line 34 (e.g., two-dimensional bar code 120b), incorporated into the handle 36 of the delivery device 30 (e.g., RFID 120d or wireless communication transmitter/receiver 120c) or any combination thereof.

The delivery device 30 may include a readable RFID module 120d. The readable RFID module 120d may attach to the exterior of the delivery device 30 (e.g., on the housing 36), as illustrated in FIG. 1, or the readable RFID module 120d may be positioned in the interior cavity formed by the housing 36. The operation of the readable RFID module 120d and the external usage tracking system 100 may be independent of the operation of the delivery device 30. As such, the readable RFID module 120d may be attached to an existing device (e.g., externally positioned) or incorporated into the delivery device 30 during the assembly process (e.g., internally or externally positioned).

In another embodiment, the internal circuitry of the delivery device 30 includes readable RFID circuitry (not explicitly shown). Internal circuitry may provide data related to the use of the delivery device 30 and send the data to the readable RFID circuitry (not explicitly shown) and the readable RFID circuitry provides at least a portion of the data related to the use of the delivery device 30 to the read module 110 of the external usage tracking system 100.

In use, the read module 110, when placed in suitable proximity to a readable RFID module 120d, receives information from the readable RFID module 120d. The information may include identification information that directly identifies the delivery device 30 or that indirectly identifies the delivery device 30 through identification of the RFID module 120d. The information may direct the read module 110 to a table, database or other data storage location that contains identification and/or usage information of the delivery device 30. For example, in some embodiments, the read module 110 receives identification information related to the readable RFID module 120d that directs the read module 110 to a database entry containing information related to the specific delivery device 30. The read module 110 may determine the compatibility between the delivery device 30 and the electrosurgical generator 20 thereby preventing use of an incompatible delivery device 30. The read module 110 may also determine if the delivery device 30 has been previously used thereby preventing reuse of a disposable product. In addition, the read module 110 may determine if the use of a limited-use reusable delivery device 30 has exceeded a maximum number of uses thereby preventing overuse of a limited-use reusable product.

After detecting the readable RFID module 120*d*, the read module 110 may verify compatibility between the delivery device 30 and the electrosurgical generator 20, may then determine various use parameters relating to the delivery device 30 and provide a signal to enable or disable the use of the electrosurgical generator 20 with the identified delivery device 30.

In some embodiments, the readable RFID module 120*d* may be connected to the energy delivery portion or control portion of the delivery device 30 such that the readable RFID module 120*d* is rendered inoperable or unreusable by the delivery device 30 when the delivery device 30 connects to, or receives electrosurgical energy from, the electrosurgical generator 20. For example, delivery device 30 may alter the information stored on the readable RFID module 120*d* or alter the operation of the readable RFID module 120*d* such that any attempt to reuse the delivery device 30 with the attached readable RFID module 120*d* would result in the external usage tracking system 100 detecting the prior use thereby preventing reuse of the delivery device 30.

Readable RFID module 120*d* may also be susceptible to one or more aspects of sterilization procedures. Exposure to a sterilization process alters information stored the readable RFID module 120*d* or the sterilization process rendering the readable RFID module 120*d* inoperable. For example, the readable RFID module 120*d* may be sensitive to heat, fluid, electromagnetic radiation and/or exposure to other conditions related to a sterilization process such that any attempt to reuse the delivery device 30 with a readable RFID module 110 that has been exposed to a sterilization process would result in detection by the external usage tracking system 100.

A packaging readable module 120*a*, with functionality related to readable modules 120*b*-120*e* discussed herein, may be incorporated into the packaging material (e.g., soft-pack 130). Packaging readable module 120*a* may be provided as an alternative to the readable modules 120*a*-120*e* positioned on the delivery device 30 or may be provided in addition to one or more readable modules 120*a*-120*e*.

In another embodiment, the packaging readable module 120*a* positioned on the packaging material (e.g., soft-pack 130) corresponds to a readable module 120*b*-120*e* associated with the delivery device 30. Read module 110 must identify the packaging readable module 120*a* and a corresponding readable module 120*b*-120*e* positioned on the delivery device 30 prior to enabling the operation of the electrosurgical generator 20.

The packaging readable module 120*a* may include a one-dimensional bar code, as illustrated in FIG. 1, incorporated into the packaging material (e.g., soft-pack 130). Prior to opening the packaging materials (e.g., soft-pack 130), the packaging readable module 120*a* may be accessible (e.g., optically scanned and/or read) by the read module 110 through one or more layers of the packaging material (e.g., soft-pack 130). The packaging readable module 120*a* is positioned on the packaging material (e.g., soft-pack 130) such that the packaging readable module 120*a* is destroyed or rendered unreadable upon opening of the packaging material (e.g., soft-pack 130).

The packaging, packaging materials and packaging techniques described herein and illustrated in the drawings should not be construed as limiting as the teachings provided herein may be utilized with, or incorporated into, other suitable surgical packages. Soft-pack 130 includes a flexible bottom layer 130*a* and a flexible top layer 130*b* connected together by an adhesive seal 132 thereby forming a sterile, interior pocket 143 therebetween. An adhesive seal 132 positioned along the edge of the flexible bottom layer 130*a* and the flexible top layer 130*b* along a first, second and third edges 131*a*-131*c* bonds the bottom layer 130*a* to the top layer 130*b*. The position of the adhesive seal 132 (e.g., inset from the fourth edge 131*d*) provides access to the individual layers of the soft-pack 130 (e.g., flexible bottom layer 130*a* and flexible top layer 130*b*). The adhesive seal 132 formed adjacent the first, second and third edges 131*a*-131*c* prevents separation between the flexible bottom and top layers 130*a* and 130*b*.

A read module 120*a*, positioned between the fourth edge 131*d* and the adhesive seal 132, is attached to the flexible top and bottom layers 130*a* and 130*b* and readable by the reader module 110 through the flexible bottom layer 130*a* and/or the flexible top layer 130*b*. The soft-pack 130 is opened by separating the flexible top and bottom layers 130*a* and 130*b* thereby breaking the adhesive seal 132 along the fourth edge 131*d*. Further separating the flexible top and bottom layers 130*a* and 130*b* breaks at least a portion of the adhesive seal 132 along the first and second edges 131*a* and 131*b*.

A readable module 120*a*, positioned between the flexible bottom and top layers 130*a* and 130*b* along the fourth edge 131*d*, includes a bond between the readable module 120*a* and each of the bottom and top layers 130*a* and 130*b*. The bond may be stronger than the material used to construct the readable module 120*a*. For example, the readable module 120*a* may be adhesively attached to the bottom and top layers 130*a* and 130*b* by an adhesive layer 131. The bond between the readable module 120*a* and each of the bottom and top layers 130*a* and 130*b* may be sufficiently strong that separating the bottom and top layers renders the readable module 120*a* non-functional (e.g., unreadable and/or unidentifiable by the read module 110).

Figure 2A:
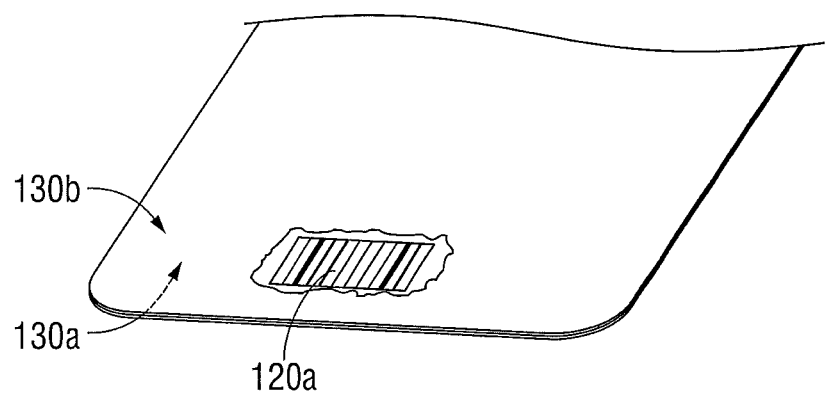
FIG. 2A is a perspective view of the packaging readable module.
Figure 2B:
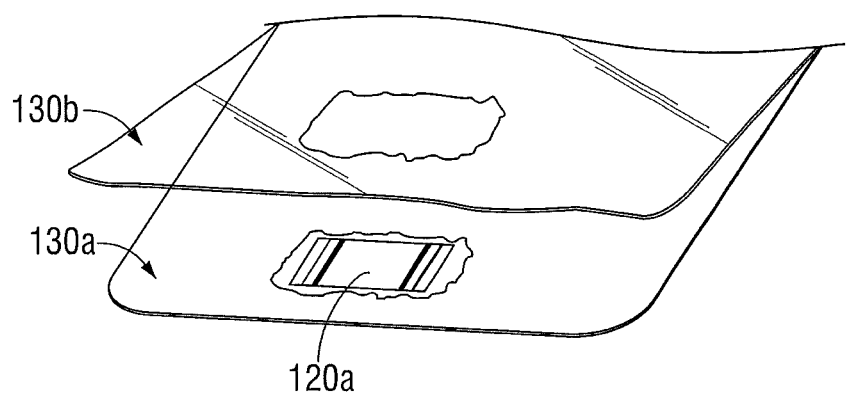
FIGS. 2B and 2C are perspective views of packaging readable modules rendered inoperable by exposure to ambient conditions.
Figure 2C:
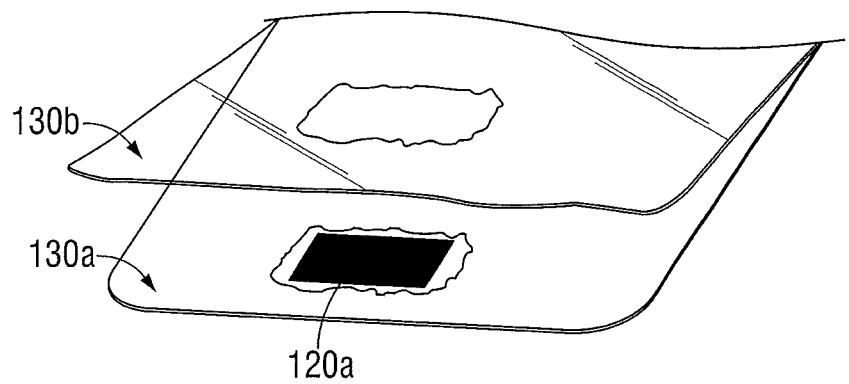
Figure 2D:
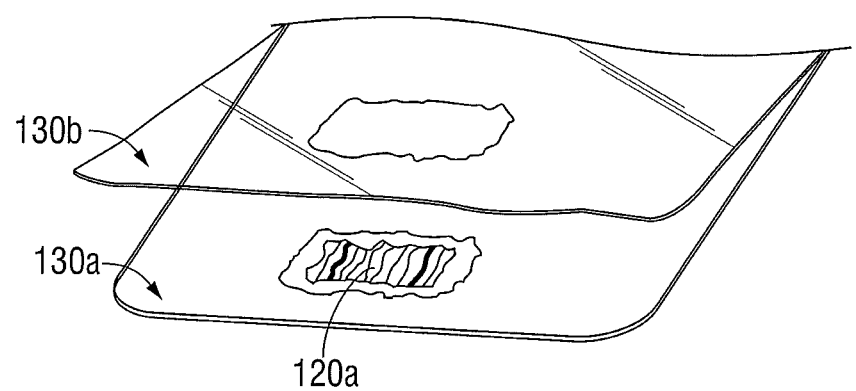
FIG. 2D is a perspective view of the packaging readable module rendered inoperable by separating the bottom layer and the top layer of the packaging materials.

In another embodiment, the readable module 120*a* is formed by bonding together the bottom and top layers 130*a* and 130*b*. As illustrated in FIG. 2D, the bottom and top layers 130*a* and 130*b* are fused together thereby forming a single layer therebetween. As such, opening the soft pack requires the destruction of the bond between the bottom and top layers 130*a* and 130*b* thereby rendering the readable module 120*a* unreadable (e.g., thereby tearing the two layers and/or stretching of the two layers thereby rendering the code unreadable).

In another embodiment, bottom and top layers 130*a* and 130*b* form a fluid-tight seal around the readable module 120*a* thereby isolating the readable module 120*a* from ambient conditions. Opening the soft-pack 130 (e.g., removing the delivery device 30) exposes the readable module 120*a* to the ambient conditions thereby rendering the readable module 120*a* non-functional and/or unreadable. For example, the readable module 120*a* may be printed with an evaporative material that evaporates when exposed to ambient conditions, as illustrated in FIG. 2B. Alternatively, as illustrated in FIG. 2C, the readable module 120*a* may include a reactive material that modifies the barcode pattern (e.g., changes the pattern of the barcode by eliminating a portion of the pattern, as illustrated in FIG. 2B, or by adding an additional portion to the pattern, as illustrated in FIG. 2C), thereby rendering the barcode unreadable.

In some embodiments, the reactive material forms at least a portion of a readable code and the reactive material reacts with one or more components in air. For example, the readable code may be formed with a solution of thymolphthalein and a base material and then sealed between the bottom and top layer 130a and 130b. When opened, the base reacts with carbon dioxide, which is always present in air, thereby dropping the pH to a level where the readable code disappears thereby rendering the packaging readable material inoperable.

In another embodiment, at least a portion of the readable code background is formed with a solution that becomes dark (e.g., reacts with air and/or oxidizes in the presents of air) when exposed to ambient conditions thereby modifying the structure of the readable code and rendering the packaging readable material inoperable.

Figure 2E:
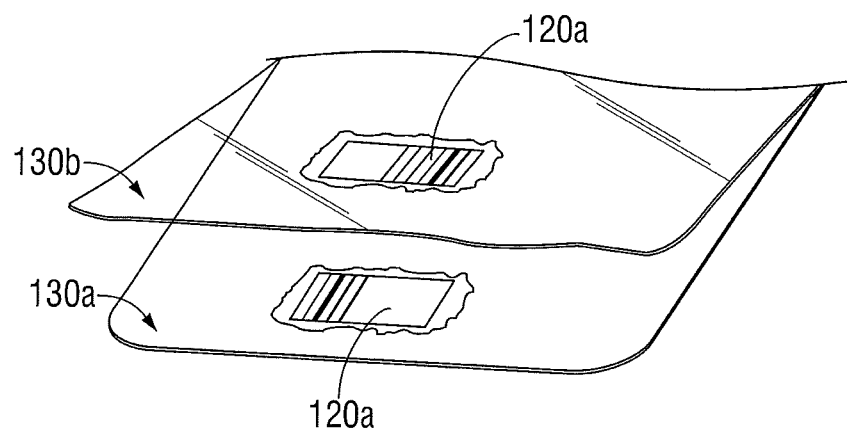
FIG. 2E is a perspective view of the packaging readable module with a portion of the packaging readable module formed on the bottom layer and a portion of the readable module formed on the top layer of the packaging materials.

In yet another embodiment, a first portion of the readable module 120a is formed on the bottom layer 130a and a second portion of the readable module 120a is formed on the top layer as illustrated in FIG. 2E. Separation of the bottom layer 120a from the top layer 130a renders the readable module 120a unreadable.

Other surgical instrument packaging arrangements may include half-shell packaging. A half-shell instrument package includes a rigid or semi-rigid bottom half-shell assembly containing at least one cavity for receiving a surgical instrument and a flexible lid portion configured to cover the cavity. A half-shell instrument package may also include a plurality of spaced apart cavities for selectively plating protective plugs at each end of the implement such that one packaging cavity may be used for a plurality of variously sized instruments. Half-shell assembly typically includes a flange area upon which the flexible lid portion adhesively attaches thereby forming a sterile cavity therebetween.

A readable module may be incorporated into the half-shell package such that separation of the flexible lid portion from the bottom half-shell assembly renders the readable module unreadable.

Yet another surgical instrument packaging arrangement includes a full-shell instrument package. A full-shell instrument package includes rigid top and bottom portions that connect in a plurality of locations thereby forming a sterile cavity for the delivery device therebetween. This type of package may be a single use package or may be resealable, and therefore reusable.

In another embodiment, a reusable delivery device 30 includes two readable modules 120 that provide information related to the specific delivery device 30. A first readable module (e.g., the packaging readable module 120a) is formed in the packaging material (e.g., soft-pack 130) and a second readable module (e.g. one of readable modules 120b-120e) is connected the reusable delivery device 30.

During the manufacturing and packaging process, the first readable module and the second readable module are provided with identification information that identifies the specific reusable delivery device 30 housed in the packaging materials.

The total use of the reusable delivery device 30 includes a first use and a finite number of subsequent permissible reuses with the final permissible use being the last permissible use.

In some embodiments, during the first use the clinician is required to identify the delivery device 30 by reading/scanning the first readable module 120a and the second readable module 120b-120e with the read module 110 of the external usage tracking system 100. The external usage and tracking system 100 determines that the delivery device 30 has not been previously used and thereby identifies the use as the first use.

The external usage and tracking system 100 may indicate an identifying feature related to the first use that further limits subsequent reuses of the delivery device 30. For example, the read module 110 may provide a location indicator that attaches to the identification information of the specific delivery device 30. The location indicator may identify the surgical facility, may identify a customer identifier, may identify a billing entity or any other information related to the specific user of the delivery device 30. The location indicator may further limit use of the specific delivery device 30 to systems and devices related to the location indicator.

In another embodiment, the packaging materials 130 may be configured for reuse with the delivery device 30. As such, each subsequent permissible use may require scanning/reading of the first readable module 120a and the second readable module 120b-120e prior to the subsequent permissible use. The delivery device 30 may be reused until the external usage and tracking system 100 determines that the current use is the last use and thereafter the delivery device 30 will be unusable. Any subsequent attempt to reuse the delivery device 30 will not be permitted by the external usage and tracking system 100.

In another embodiment, the packaging materials 130 are not reusable and intended to be discarded after the first use. As such, each subsequent permissible use only requires scanning/reading of the second readable module 120b-120e. The delivery device 30 may be reused until the external usage and tracking system 100 determines that the current use is the last use and thereafter the delivery device 30 will be unusable. Any subsequent attempt to reuse the delivery device 30 will not be permitted by the external usage and tracking system 100.

A subsequent scan of the first readable module 120a would indicate that packaging materials 130 that were not intended for reuse were reused and may indicate improper sterilization procedures. Reuse of the delivery device 30 may be prohibited or prevented. Alternatively, the rescanning of a first readable module 120a on a subsequent permissible use may generate an indicator or alarm that proper sterilization procedures were not performed at the identified location or performed by the identified user.

In yet another embodiment, the external usage and tracking system 100 as described herein, is incorporated into a sterilization system. For example, the electrosurgical system 20, as illustrated in FIG. 1, may be a sterilization system 20 that sterilizes the delivery device and prepares the delivery device for a subsequent use as discussed hereinabove. The sterilization system 20 provides information related to the sterilization of the delivery device, either directly or indirectly through read module 120, to the device tracking and management system 115.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. A system for tracking use of a medical device, comprising:
   an electrosurgical generator configured to selectively deliver an electrosurgical energy signal to an electrosurgical delivery device;
   a packaging system configured to house the electrosurgical delivery device;
   a packaging readable module connected to the packaging system and configured to uniquely identify the electrosurgical delivery device housed in the packaging system, wherein the packaging readable module is formed between a first layer and a second layer of the packaging system, the packaging readable module including an evaporative material that evaporates when exposed to ambient conditions, exposure of the packaging readable module to the ambient conditions renders the packaging readable module inoperable such that the packaging readable module is rendered inoperable by separating the first and second layers when the electrosurgical delivery device is removed from the packaging system; and a read module in communication with the electro surgical generator and configured to identify the packaging readable module and further configured to determine the viability of the electro surgical delivery device;

wherein delivery of the electro surgical energy signal to the electro surgical delivery device is enabled by the read module if the electrosurgical delivery device is a viable device.

2. The system according to claim 1, wherein the first layer and the second layer of the packaging system form an air-tight seal around the packaging readable module thereby preventing the packaging readable module from exposure to the ambient conditions.

3. The system according to claim 1, wherein the packaging readable module includes a readable code and the readable code includes a reactive material that modifies the readable code when exposed to the ambient conditions.

4. The system according to claim 1, wherein a first portion of the packaging readable module is formed on the first layer of the packaging system and a second portion of the packaging readable module is formed on the second layer of the packaging system.

5. The system according to claim 1, further including:
a device tracking and management system in communication with the read module and configured to provide information specific to the uniquely identified electrosurgical delivery device to the read module,
wherein the read module determines the viability of the electrosurgical delivery device based on the information specific to the uniquely identified electrosurgical delivery device provided from the device tracking and management system.

6. The system according to claim 5, wherein the read module provides information relating to the electrosurgical generator to the device tracking and management system.

7. The system according to claim 6, wherein the device tracking and management system includes a billing module configured to generate a per use bill based on the information related to the electro surgical generator provided by the read module.

8. The system according to claim 6, wherein the device tracking and management system includes an inventory control module configured to maintain product inventory based on the information related to the electrosurgical generator provided by the read module.

9. The system according to claim 1, wherein the packaging readable module includes memory accessible by the read module when the read module electrically connects to the memory.

10. The system according to claim 1, wherein the packaging readable module further includes a readable code and the read module includes a scanner configured to identify the readable code.

11. The system according to claim 10, wherein the scanner is a camera.

12. The system according to claim 1, wherein the packaging readable module includes a radio frequency identification module and the read module includes a scanner configured to identify the radio frequency identification module.

13. A system for tracking use of a medical device, comprising:
an electro surgical generator configured to selectively deliver an electro surgical energy signal to an electro surgical delivery device;
a packaging system configured to house the electrosurgical delivery device;
a packaging readable module connected to the packaging system and configured to uniquely identify the electrosurgical delivery device housed in the packaging system, wherein a first layer and a second layer of the packaging system form an air-tight seal around the packaging readable module thereby preventing the packaging readable module from exposure to ambient conditions, wherein the packaging readable module includes a readable code and the readable code includes a reactive material that modifies the readable code when exposed to the ambient conditions, exposure of the packaging readable module to the ambient conditions renders the packaging readable module inoperable such that the packaging readable module is rendered inoperable when the electrosurgical delivery device is removed from the packaging system; and
a read module in communication with the electrosurgical generator and configured to identify the packaging readable module and further configured to determine the viability of the electro surgical delivery device;
wherein delivery of the electro surgical energy signal to the electro surgical delivery device is enabled by the read module if the electrosurgical delivery device is a viable device.

* * * * *